(12) United States Patent
Nessel et al.

(10) Patent No.: US 10,737,039 B2
(45) Date of Patent: Aug. 11, 2020

(54) MEDICAMENT DELIVERY DEVICE AND CARTRIDGE

(71) Applicant: Sanofi-Aventis Deutschland GMBH, Frankfurt am Main (DE)

(72) Inventors: Christian Nessel, Frankfurt am Main (DE); Charley Henderson, Frankfurt am Main (DE); David Cross, Frankfurt am Main (DE); Douglas Ivan Jennings, Frankfurt am Main (DE); Ryan Anthony McGinley, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 300 days.

(21) Appl. No.: 15/610,107

(22) Filed: May 31, 2017

(65) Prior Publication Data
US 2017/0304559 A1    Oct. 26, 2017

Related U.S. Application Data

(62) Division of application No. 14/433,337, filed as application No. PCT/EP2013/070459 on Oct. 1, 2013, now Pat. No. 9,700,683.

(30) Foreign Application Priority Data

Oct. 4, 2012    (EP) .................................. 12187312

(51) Int. Cl.
*A61M 5/50*    (2006.01)
*A61M 5/168*   (2006.01)
*A61M 5/145*   (2006.01)

(52) U.S. Cl.
CPC ........ *A61M 5/5086* (2013.01); *A61M 5/1452* (2013.01); *A61M 5/1456* (2013.01);
(Continued)

(58) Field of Classification Search
CPC .. A61M 2205/6063; A61M 2205/3313; A61M 5/16831; A61M 5/1684; G01F 23/292
See application file for complete search history.

(56) References Cited

U.S. PATENT DOCUMENTS

2009/0299279 A1    12/2009  Richter
2013/0310756 A1*   11/2013  Whalley ................. A61M 5/31
                                              604/189
(Continued)

FOREIGN PATENT DOCUMENTS

JP    3316213        2/1994
JP    2005/506852    3/2005
(Continued)

OTHER PUBLICATIONS

Extended European Search Report in Application No. 12187312.9, dated Apr. 2, 2013, 8 pages.
(Continued)

*Primary Examiner* — Emily L Schmidt
(74) *Attorney, Agent, or Firm* — Fish & Richardson P.C.

(57) ABSTRACT

Described is a cartridge comprising a body adapted to contain a medicament, a bung slidably disposed in the body and having a distal face and a proximal face, and a light element coupled to a component of the cartridge. Further described is a medicament delivery device comprising the cartridge, a first receiver adapted to receive an optical signal from the light element and convert the optical signal into a first electrical signal, and a second receiver adapted to receive an optical signal from the light element and convert the optical signal into a second electrical signal.

16 Claims, 3 Drawing Sheets

(52) U.S. Cl.
CPC .... *A61M 5/14566* (2013.01); *A61M 5/16804* (2013.01); *A61M 5/16831* (2013.01); *A61M 5/16877* (2013.01); *A61M 2205/3306* (2013.01); *A61M 2205/702* (2013.01)

(56) References Cited

U.S. PATENT DOCUMENTS

| | | | | |
|---|---|---|---|---|
| 2013/0336814 | A1* | 12/2013 | Kamen | A61M 5/16859 417/302 |
| 2015/0250955 | A1 | 9/2015 | Nessel et al. | |

FOREIGN PATENT DOCUMENTS

| | | |
|---|---|---|
| JP | 2005/533568 | 11/2005 |
| JP | 2008/17995 | 1/2008 |
| JP | 2008/17995 | 8/2009 |
| JP | 2010/0505475 | 2/2010 |
| WO | WO 2002/056934 | 7/2002 |
| WO | WO 2008/040479 | 4/2008 |
| WO | WO 2011/032960 | 3/2011 |

OTHER PUBLICATIONS

International Preliminary Report on Patentability in International Application No. PCT/EP2013/070459, dated Apr. 7, 2015, 8 pages.
International Search Report and Written Opinion in International Application No. PCT/EP2013/070459, dated Oct. 29, 2013, 10 pages.
Von Horst Kuchling, "Lichtstrahlung," Taschenbuch Der Physik, pp. 404-415 (2004).
Japanese Office Action in Application No. 2015-534987, dated Jul. 4, 2017, 9 pages.

\* cited by examiner

MEDICAMENT DELIVERY DEVICE AND CARTRIDGE

This application is a divisional of U.S. application Ser. No. 14/433,337, filed Apr. 2, 2015, which is a 371 U.S. National Application of PCT/EP2013/070459, filed on Oct. 1, 2013, which claims priority to European Patent Application Nos. 12187312.9, filed on Oct. 4, 2012, the entire contents of which are incorporated herein by reference.

TECHNICAL FIELD

The invention relates to medicament delivery device and a cartridge.

BACKGROUND OF THE INVENTION

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Conventional autoinjectors have limited safety features and compliance features. For example, some conventional autoinjectors may continue dispensing the medicament even when the autoinjector is removed from the injection site. Thus, it cannot be determined whether the patient received an intended dose.

Conventional delivery devices may also have limited feedback mechanisms. For example, some conventional delivery devices may provide audible feedback only, when an injection is initiated and/or completed.

Conventional injection devices may deliver the entire contents of a syringe/cartridge or may provide a predetermined or set dose. Conventional injection devices can lack mechanisms to ensure accurate dose delivery. For example, when the entire contents of the syringe/cartridge are intended to be delivered, a residual amount may remain which either means that a full dose was not delivered or the syringe/cartridge must be overfilled to ensure a proper dose is administered. As a further example, when the predetermined/set dose is delivered, over- or under-dosing may occur.

Thus, there remains a need for an improved medicament delivery device and cartridge.

SUMMARY OF THE INVENTION

It is an object of the present invention to provide an improved medicament delivery device and cartridge.

In an exemplary embodiment, a cartridge according to the present invention comprises a body adapted to contain a medicament, a bung slidably disposed in the body and having a distal face and a proximal face, and a light element coupled to a component of the cartridge.

In an exemplary embodiment, the light element is coupled to the proximal face of the bung. The light element is wholly or partially embedded in the bung.

In an exemplary embodiment, the light element is coupled to the body.

In an exemplary embodiment, the cartridge further comprises a power source electrically, inductively or radio frequency coupled to the light element.

In an exemplary embodiment, the light element is a light emitting device or a light reflecting device.

In an exemplary embodiment, the bung is translucent or made of a light reflecting material.

In an exemplary embodiment, the cartridge further comprises a lens disposed adjacent the light element.

In an exemplary embodiment, a medicament delivery device according to the present invention comprises the cartridge, a first receiver adapted to receive an optical signal from the light element and convert the optical signal into a first electrical signal, and a second receiver adapted to receive an optical signal from the light element and convert the optical signal into a second electrical signal.

In an exemplary embodiment, the delivery device further comprises a light source disposed adjacent the first receiver and the second receiver. The light source is adapted to emit light toward the light element.

In an exemplary embodiment, the first receiver and the second receiver are radially offset by a radial distance from a longitudinal axis of the delivery device.

In an exemplary embodiment, the first receiver and the second receiver are axially offset by an axial distance.

In an exemplary embodiment, the first receiver is arranged a first minimum axial distance from a reference line and the second receiver is arranged a second minimum axial distance from the reference line. The reference line corresponds to an axial position of the light element prior to use of the medicament delivery device.

In an exemplary embodiment, the delivery device further comprises a controller adapted to compute a displacement of the light element relative to the reference line using the first and second electrical signals. The controller is adapted to compute a dose of medicament delivered or a needle position based on the displacement. The controller computes the displacement as follows:

$$I = \left[\frac{r_1 - r_2}{\left(\sqrt{\frac{\cos\alpha}{E_1}} - \sqrt{\frac{\cos\alpha}{E_2}}\right)}\right]^2$$

$$r = \sqrt{\frac{I * \cos\alpha}{E_1}}$$

where E1 illumination value at first receiver;
E2 illumination value at second receiver;
I total illumination;
α angle of diffusion of light from the light element relative to the longitudinal axis;
r displacement of light element relative to the reference line;
r1 first minimum axial distance between the light element and the first receiver when the light element is positioned at the reference line; and
r2 second minimum axial distance between the light element and the second receiver when the light element is positioned at the reference line.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-N H2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(02)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (02)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(02)25, Asp28] Exendin-4(S1-39)-(Lys)6-NH2,
H-Asn-(Glu)5-des Pro36, Pro37, Pro38 [Met(O)14, Trp (02)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by $\alpha, \beta, \epsilon, \gamma$, and $\mu$. The type of heavy chain present defines the isotype of antibody; these chains are found in IgA, IgD, IgE, IgG, and IgM antibodies, respectively.

Distinct heavy chains differ in size and composition; $\alpha$ and $\gamma$ contain approximately 450 amino acids and $\delta$ approximately 500 amino acids, while $\mu$ and $\epsilon$ have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains $\gamma, \alpha$ and $\delta$ have a constant region composed of three tandem Ig domains, and a hinge region for added flexibility; heavy chains $\mu$ and $\epsilon$ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by $\lambda$ and $\kappa$. A light chain has two successive domains: one constant domain (CL) and one variable domain (VL). The approximate length of a light chain is 211 to 217 amino acids. Each antibody contains two light chains that are always identical; only one type of light chain, $\kappa$ or $\lambda$, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
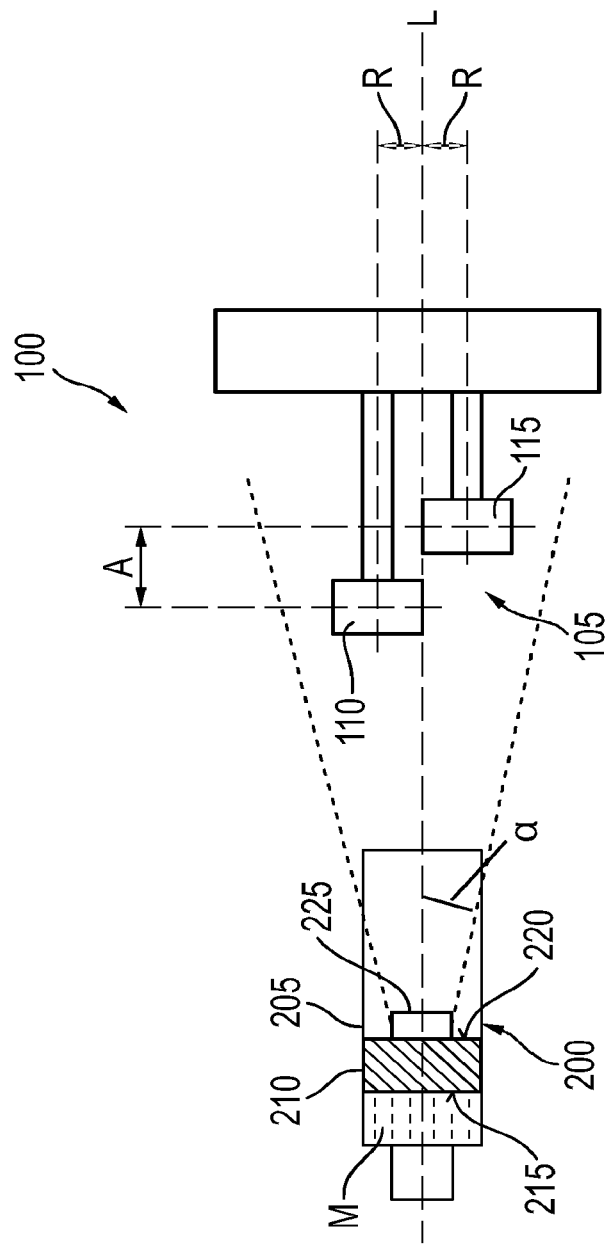
FIG. 1 shows an exemplary embodiment of a medicament delivery device and cartridge according to the present invention.

FIG. 1 shows an exemplary embodiment of a medicament delivery device 100 and cartridge 200 according to the present invention. The delivery device 100 may be any type of injection device which is used to inject a medicament from a syringe or cartridge. Those of skill in the art will understand that such injection devices include, but are not limited to, pen injectors, pre-filled syringes, autoinjectors, perfusion devices, infusion devices, etc. Further, the medicament delivery device 100 according to the present invention may be embodied as an attachment to a pre-existing injection device. For example, the delivery device 100 may be a cap-type attachment which is removably coupled to an injection device and can be reused.

In the exemplary embodiment, the delivery device 100 may include components common to conventional delivery devices such as, for example, one or more springs, plungers, needle shields, syringe/cartridge carriers, etc.

In the exemplary embodiment shown in FIG. 1, the delivery device 100 includes an optical system 105 comprising a first receiver 110 and a second receiver 115. In the exemplary embodiment, the receivers 110, 115 are photodiodes, phototransistors, photomulipliers, etc. capable of receiving an optical signal (e.g., light) and converting the optical signal into an electrical signal. In the exemplary embodiment, the receivers 110, 115 are arranged in parallel in the delivery device 100 and are spaced apart axially by an axial offset A and radially by a radial offset R from a longitudinal axis L of the delivery device 100. While the exemplary embodiment depicts only two receivers, those of skill in the art will understand that more than two receivers may be utilized.

The exemplary embodiment of the cartridge 200 shown in FIG. 1 includes a body 205 containing a medicament M and a bung 210 slidably disposed in the body 205. The bung 210 has a distal face 215 in contact with the medicament M and a proximal face 220. In an exemplary embodiment, a light element 225 is coupled to the cartridge 200. For example, the light element 225 may be coupled to the proximal face 220 of the bung 210, e.g., embedded wholly or partially in the bung 210 or disposed on the proximal face 220 (e.g., via an adhesive, clamping or welding). In another exemplary embodiment, the light element 225 may be disposed on the body 205. In other exemplary embodiments, more than one light element 225 may be disposed on the cartridge 200, and in the case of a plurality of light elements 225, each light element 225 may emit a different wavelength of light. In a further exemplary embodiment, the light element 225 may be disposed on a component (e.g., a carrier) which is coupled to the cartridge 200. For example, the cartridge 200 may be placed in a carrier which is slidably disposed in the delivery device 100. Thus, movement of the carrier may correspond directly to movement of the cartridge 200.

Figure 2:
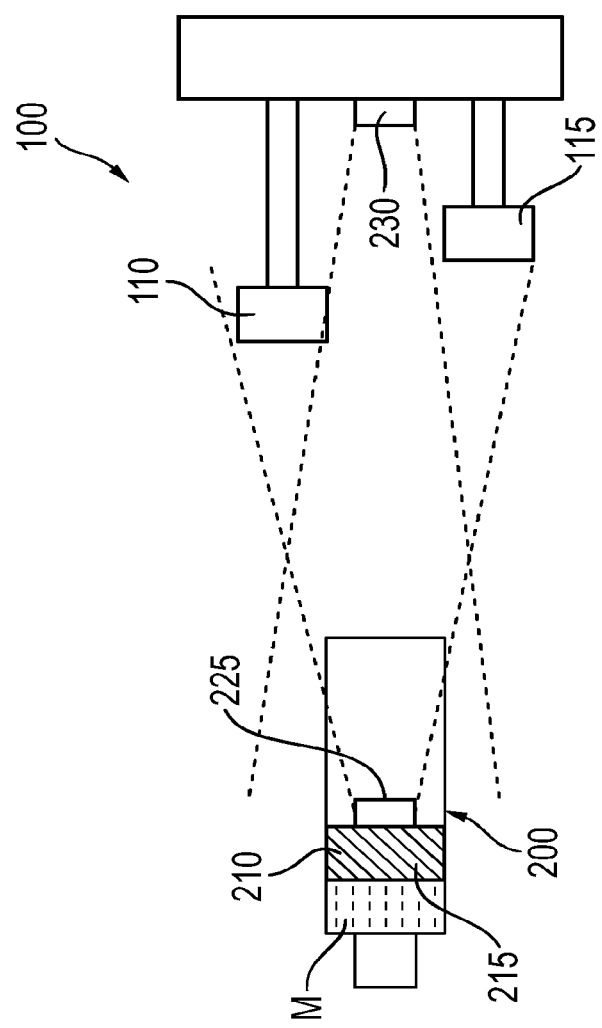
FIG. 2 shows another exemplary embodiment of a medicament delivery device and cartridge according to the present invention.

In the exemplary embodiment shown in FIG. 1, the light element 225 is a light emitting device, e.g., a light emitting diode (LED). In the exemplary embodiment shown in FIG. 2, the light element 225 is a light reflecting device, e.g., a mirror. In the embodiment shown in FIG. 2, a light source 230 may be disposed on the delivery device 100 and focused toward the light element 225. For example, the light source 230 may be positioned between the receivers 110, 115. One or more reflectors or lenses may be positioned adjacent the light element 225 to focus and/or direct light emitting from the light element 225. If the light element 225 requires a power source (not shown) such as a battery, it may be electrically, inductively or radio frequency coupled to the light element 225.

As explained further herein, displacement and direction of displacement of the bung 215 and/or the cartridge 200 may be determined by analyzing the optical signals from the light element 225 which are received by the receivers 110, 115.

Figure 3:
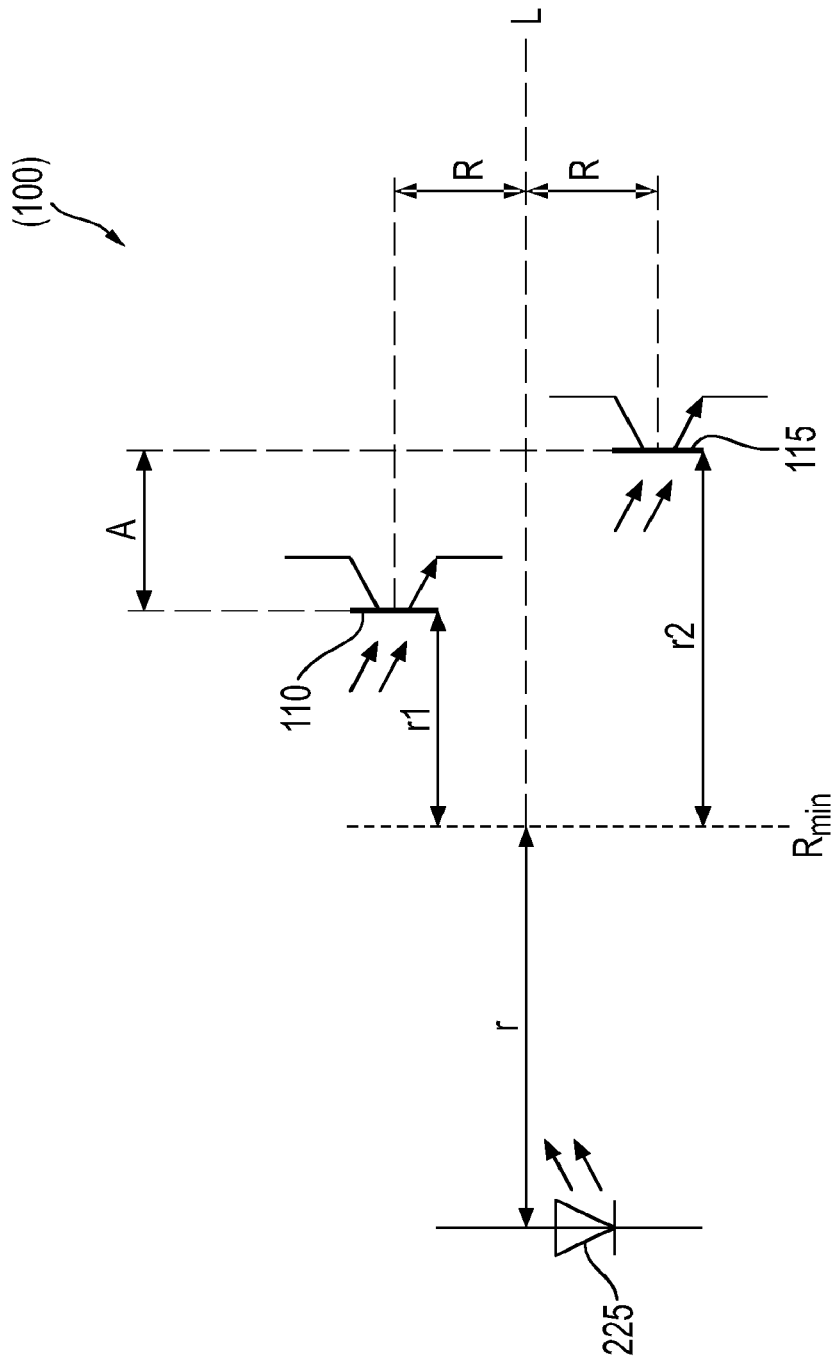
FIG. 3 shows a logical view of a medicament delivery device and cartridge according to the present invention.

FIG. 3 shows a logical view of an exemplary embodiment of a medicament delivery device and cartridge according to the present invention. As noted above, the receivers 110, 115 are spaced apart axially by an axial offset A and radially by a radial offset R from the longitudinal axis L of the delivery device 100. A reference line $R_{min}$ is designed to be a most proximal position (e.g., pre-use position) of the light element 225 in the delivery device 100, and a first minimum axial distance r1 between the light element 225 and the first receiver 110 and a second minimum axial distance r2 between the light element 225 and the second receiver 115. A displacement r of the light element 225 away from the reference line $R_{min}$ can be determined by analyzing the optical signals received by the receivers 110, 115. The displacement r may then be utilized by, for example, a controller in the delivery device 100 to compute an amount of the medicament delivered, to operate other mechanisms (e.g., user interface, feedback, needle safety, etc.) of the delivery device 100.

In an exemplary embodiment, the controller in the delivery device 100 may utilize the following formulas to compute illumination values at each of the receivers 110, 115 to determine the displacement r.

A luminance intensity dispersion formula (1) shown below solves for an illumination value E (in lux) which corresponds to the specific illumination value received at each of the receivers 110, 115. Formula (1) is discussed in Kuchling, H., "Taschenbuch der Physik," Carl Hanser Verlag, 2004, which is incorporated by reference herein.

$$E = \frac{I * \cos\alpha}{r^2} E:[lx]; \ I:[cd]; \ r:[m] \quad (1)$$

To solve for the illumination values E1 and E2 at the first receiver 110 and the second receiver 115, respectively, the following formulas can be used:

$$E_1 = \frac{I * \cos\alpha}{(r + r_1)^2} \quad (2)$$

$$E_2 = \frac{I * \cos\alpha}{(r + r_2)^2} \quad (3)$$

where E1 illumination value at first receiver 110
E2 illumination value at second receiver 115
I total illumination
α angle of diffusion of light from the light element 225 relative to the longitudinal axis L r displacement of light element 225 relative to the reference line $R_{min}$ r1 first minimum axial distance r1 between the light element 225 and the first receiver 110 (e.g., when the light element 225 is positioned at the reference line $R_{min}$)

Both formulas can be transformed to solve for the displacement r:

$$\frac{E_1}{I * \cos \alpha} = \frac{1}{(r+r_1)^2} \quad (4)$$

$$\frac{I * \cos \alpha}{E_1} = (r+r_1)^2 \quad (5)$$

$$\sqrt{\frac{I * \cos \alpha}{E_1}} = r + r_1 \quad (6)$$

$$\sqrt{\frac{I * \cos \alpha}{E_1}} - r_1 = r \quad (7)$$

$$\frac{E_2}{I * \cos \alpha} = \frac{1}{(r+r_2)^2} \quad (8)$$

$$\frac{I * \cos \alpha}{E_2} = (r+r_2)^2 \quad (9)$$

$$\sqrt{\frac{I * \cos \alpha}{E_2}} = r + r_2 \quad (10)$$

$$\sqrt{\frac{I * \cos \alpha}{E_2}} - r_2 = r \quad (11)$$

Both formulas can be used to solve for the total illumination I:

$$\sqrt{\frac{I * \cos \alpha}{E_1}} - r_1 = \sqrt{\frac{I * \cos \alpha}{E_2}} - r_2 \quad (12)$$

$$\sqrt{\frac{I * \cos \alpha}{E_1}} - \sqrt{\frac{I * \cos \alpha}{E_2}} = r_1 - r_2 \quad (13)$$

$$\sqrt{I} * \left( \sqrt{\frac{\cos \alpha}{E_1}} - \sqrt{\frac{\cos \alpha}{E_2}} \right) = r_1 - r_2 \quad (14)$$

$$\sqrt{I} = \frac{r_1 - r_2}{\left( \sqrt{\frac{\cos \alpha}{E_1}} - \sqrt{\frac{\cos \alpha}{E_2}} \right)} \quad (15)$$

$$I = \left[ \frac{r_1 - r_2}{\left( \sqrt{\frac{\cos \alpha}{E_1}} - \sqrt{\frac{\cos \alpha}{E_2}} \right)} \right]^2 \quad (16)$$

Formula (16) describes a differential measurement based on the recorded intensity by each receiver 110, 115. The total illumination I can then be used to solve for the displacement r:

$$E_1 = \frac{I * \cos \alpha}{r^2} \quad (18)$$

$$r^2 = \frac{I * \cos \alpha}{E_1} \quad (19)$$

$$r = \sqrt{\frac{I * \cos \alpha}{E_1}} \quad (20)$$

When the light element 225 is coupled to the bung 210, based on the displacement r, the controller can, for example, determine a dose of the medicament delivered, activate a safety mechanism (e.g., a needle shield), activate a user feedback mechanism (e.g., audible, tactile, visual), etc.

When the light element 225 is coupled to the body 205, based on the displacement r, the controller can, for example, determine a position of a needle (e.g., needle penetration depth, needle retraction), activate a safety mechanism (e.g., a needle shield), activate a user feedback mechanism (e.g., audible, tactile, visual), etc.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A cartridge comprising:
    a body configured to contain a medicament;
    a bung slidably disposed in the body, the bung having a distal face and a proximal face, the distal face configured to be in contact with the medicament; and
    a light emitting device directly coupled to the proximal face of the bung, the light emitting device configured to direct light proximally along a longitudinal axis of the body, the light having an angle of diffusion relative to the longitudinal axis such that the light is received at a location proximal to the light emitting device and transversally offset from the longitudinal axis.

2. The cartridge of claim 1, wherein the light emitting device is configured to direct the light proximally to locations proximal to the light emitting device such that illuminance values at the locations are indicative of an axial displacement of the bung.

3. The cartridge of claim 2, wherein the illuminance values at the locations are indicative of a dose of medicament delivered from the cartridge.

4. The cartridge of claim 1, wherein the light emitting device is wholly embedded in the bung.

5. The cartridge of claim 1, wherein the light emitting device is coupled to the body.

6. The cartridge of claim 1, further comprising a power source coupled to the light emitting device.

7. The cartridge of claim 1, wherein the bung is translucent.

8. The cartridge of claim 1, further comprising a lens disposed adjacent the light emitting device, the lens configured to focus an optical signal emitted by the light emitting device.

9. The cartridge of claim 1, wherein the light emitting device is configured such that the light is received at locations proximal to the light emitting device, transversally offset from one another, and transversally offset from the longitudinal axis.

10. The cartridge of claim 1, wherein the light is diffuse light.

11. The cartridge of claim 1, further comprising the medicament, the medicament comprising at least one pharmaceutically active compound.

12. The cartridge of claim 1, wherein the light emitting device is positioned to direct the light such that an illuminance of the light at a reference line perpendicular to a longitudinal axis of the cartridge decreases as the bung advances through the cartridge.

13. The cartridge of claim 12, wherein the bung is configured to be positioned at the reference line prior to use of the cartridge.

14. The cartridge of claim 1, wherein the light emitting device is configured to direct the light in a direction substantially parallel to the longitudinal axis.

15. A cartridge comprising:
a body configured to contain a medicament;
a bung slidably disposed in the body, the bung having a distal face and a proximal face, the distal face configured to be in contact with the medicament; and
a light emitting device directly coupled to the proximal face of the bung, the light emitting device configured to direct light proximally along a longitudinal axis of the body, the light having an angle of diffusion relative to the longitudinal axis such that the light is received at locations proximal to the light emitting device, proximal to the bung, transversely offset from one another, and transversally offset from the longitudinal axis.

16. A cartridge comprising:
a body configured to contain a medicament;
a bung slidably disposed in the body, the bung having a distal face and a proximal face, the distal face configured to be in contact with the medicament; and
a light emitting device directly coupled to the proximal face of the bung, the light emitting device configured to direct light proximally along a longitudinal axis of the body and proximal to the bung, the light having an angle of diffusion relative to the longitudinal axis such that the light is received at a location proximal to the light emitting device, proximal to the bung, and transversally offset from the longitudinal axis,
wherein the light is diffuse light.

* * * * *